United States Patent
Amin et al.

(10) Patent No.: US 10,420,502 B2
(45) Date of Patent: *Sep. 24, 2019

(54) OPTIMIZED INDIVIDUAL SLEEP PATTERNS

(71) Applicant: INTERNATIONAL BUSINESS MACHINES CORPORATION, Armonk, NY (US)

(72) Inventors: Mahmoud Amin, Poughkeepsie, NY (US); Zhenxing Bi, Niskayuna, NY (US); Lawrence A. Clevenger, Rhinebeck, NY (US); Leigh Anne H. Clevenger, Rhinebeck, NY (US); Krishna R. Tunga, Wappingers Falls, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/801,720

(22) Filed: Nov. 2, 2017

(65) Prior Publication Data

US 2018/0368757 A1      Dec. 27, 2018

Related U.S. Application Data

(63) Continuation of application No. 15/631,064, filed on Jun. 23, 2017.

(51) Int. Cl.
*A61B 5/00* (2006.01)
*G16H 50/20* (2018.01)
(Continued)

(52) U.S. Cl.
CPC .......... *A61B 5/4815* (2013.01); *A61B 5/0022* (2013.01); *A61B 5/1118* (2013.01);
(Continued)

(58) Field of Classification Search
CPC ..................................... G06F 9/44; G06F 1/32
See application file for complete search history.

(56) References Cited

U.S. PATENT DOCUMENTS 6,902,296 B2    6/2005   Searfoss, III
7,001,611 B2    2/2006   Kiso et al.
(Continued)

OTHER PUBLICATIONS

Mahmoud Amin et al., "Optimized Individual Sleep Patterns", Related Application; U.S. Appl. No. 15/631,064, filed Jun. 23, 2017.
(Continued)

*Primary Examiner* — Jaweed A Abbaszadeh
*Assistant Examiner* — Keshab R Pandey
(74) *Attorney, Agent, or Firm* — Cantor Colburn LLP; Vazken Alexanian

(57) ABSTRACT

Embodiments of the invention are directed to a computer-implemented method for generating a sleep optimization plan. A non-limiting example of the computer-implemented method includes receiving, by a processor, genetic data for a user. The method also includes receiving, by the processor, Internet of Things (IoT) device data for the user. The method also includes generating, by the processor, a sleep duration measurement for the user based at last in part upon the IoT device data. The method also includes generating, by the processor, a sleep optimization plan for the user based at least in part upon the genetic data.

12 Claims, 7 Drawing Sheets

(51) Int. Cl.
  *G16H 15/00* (2018.01)
  *G16H 20/30* (2018.01)
  *G16H 10/60* (2018.01)
  *G16H 40/63* (2018.01)
  *A61B 5/11* (2006.01)

(52) U.S. Cl.
  CPC .............. *A61B 5/1123* (2013.01); *A61B 5/68* (2013.01); *G16H 10/60* (2018.01); *G16H 15/00* (2018.01); *G16H 20/30* (2018.01); *G16H 40/63* (2018.01); *G16H 50/20* (2018.01); *A61B 5/00* (2013.01); *A61B 5/681* (2013.01); *A61B 5/6898* (2013.01)

(56) References Cited

U.S. PATENT DOCUMENTS

| | | | |
|---|---|---|---|
| 2008/0317835 A1 | 12/2008 | Azimi et al. | |
| 2010/0099954 A1* | 4/2010 | Dickinson | A61B 5/0006 600/300 |
| 2010/0202972 A1* | 8/2010 | Winkelmann | C07K 14/47 424/9.2 |
| 2014/0184414 A1* | 7/2014 | Matsumoto | G06F 19/3481 340/575 |
| 2014/0371256 A1 | 12/2014 | Sadhasivam et al. | |
| 2016/0051184 A1 | 2/2016 | Wisbey et al. | |
| 2016/0151603 A1* | 6/2016 | Shouldice | H04R 3/00 600/28 |
| 2016/0192218 A1* | 6/2016 | Peters | A61B 5/4815 370/252 |
| 2016/0206240 A1 | 7/2016 | Oakhill | |
| 2016/0364549 A1 | 12/2016 | Wei et al. | |
| 2018/0261329 A1* | 9/2018 | Blander | G16H 50/30 |
| 2018/0286520 A1* | 10/2018 | Apte | G16H 10/40 |
| 2018/0368756 A1 | 12/2018 | Amin | |

OTHER PUBLICATIONS

List of IBM Patents or Patent Applications Treated as Related; (Appendix P), Filed Nov. 2, 2017; pp. 1-2.

Bachmann et al., "Functional ADA polymorphism increases sleep depth and reduces vigilant attention in humans," Cerebral Cortex, 2011, bhr173, 9 pages.

Sonka et al., "Past and present in drug treatment of sleep disorders," Neuroendocrinology Letters, vol. 35, No. 3, 2014, pp. 186-197.

List of IBM Patents or Patent Applications Treated as Related; (Appendix P), Date filed Mar. 19, 2019; pp. 1-2.

* cited by examiner

OPTIMIZED INDIVIDUAL SLEEP PATTERNS

DOMESTIC AND/OR FOREIGN PRIORITY

This application is a continuation of U.S. application Ser. No. 15/631,064, titled "Optimized Individual Sleep Patterns" filed Jun. 23, 2017, the contents of which are incorporated by reference herein in its entirety.

BACKGROUND

The present invention relates in general to sleep patterns, and more specifically to optimized individual sleep patterns.

The duration and quality of sleep can impact a number of factors pertaining to health and well-being. A sufficient amount of sleep, for example, is required for optimal brain function and attention. For instance, even relatively minor sleep deficits can lead to underperformance at work or school. It has been shown, for example, that missing only one to two hours of sleep can as much as double the risk of a car accident. Sleep is not only associated with brain function and attention, but can also be linked with proper immune system functioning, obesity, and mood.

Optimizing sleep patterns to provide optimal recommendations for health and well-being can be challenging. Sleep quality and duration, for example, can be highly individualized. It is frequently observed, for example, that the sheer number of hours of sleep required for an individual to consider him or herself rested varies from person to person. Moreover, sleep duration and quality can be affected by external factors and biological factors. For example, research indicates that exposure to light not only during sleeping hours, but also in the hours preceding sleep, can adversely impact sleep quality.

Measuring the quality and duration of sleep can also pose a number of challenges. For example, movement-based sensors worn by individuals can in some cases distinguish between periods of wakefulness and sleep, but can be subject to erroneous readings when individuals move during sleep. In addition, the degree and duration of movement during sleep can also vary from person to person, further complicating motion-based sleep measurements.

SUMMARY

Embodiments of the invention are directed to a computer-implemented method for generating a sleep optimization plan. A non-limiting example of the computer-implemented method includes receiving, by a processor, genetic data for a user. The method also includes receiving, by the processor, Internet of Things (IoT) device data for the user. The method also includes generating, by the processor, a sleep duration measurement for the user based at last in part upon the IoT device data. The method also includes generating, by the processor, a sleep optimization plan for the user based at least in part upon the genetic data. Such embodiments can provide personalized sleep optimization for an individual to improve overall health and well-being.

Embodiments of the invention are directed to a computer program product for generating a sleep optimization plan. The computer program product includes a computer readable storage medium readable by a processing circuit and storing program instructions for execution by the processing circuit for performing a method. A non-limiting example of the method includes receiving genetic data for a user. The method also includes receiving IoT device data for the user. The method also includes generating a sleep duration measurement for the user based at last in part upon the IoT device data. The method also includes generating a sleep optimization plan for the user based at least in part upon the genetic data. Such embodiments can provide personalized sleep optimization for an individual to improve overall health and well-being.

Embodiments of the invention are directed to a processing system for generating a sleep optimization plan. The processor is in communication with one or more types of memory. In a non-limiting example of the processing system, the processor is configured to receive genetic data for a user. The processor is also configured to receive IoT device data for the user. The processor is also configured to generate a sleep duration measurement for the user based at last in part upon the IoT device data. The processor is also configured to generate a sleep optimization plan for the user based at least in part upon the genetic data. Such embodiments can provide personalized sleep optimization for an individual to improve overall health and well-being.

Embodiments of the invention are directed to a computer-implemented method for generating a sleep duration estimate. A non-limiting example of the computer-implemented method includes receiving by a processor, sleep-motion genetic data for a user. The method also includes sensing, by a motion sensor in an IoT network, user motion. The method also includes generating, by the processor, a preliminary wakeful period identification based at least in part upon the sensed user motion. The method also includes generating, by the processor, a corrected wakeful period identification based at least in part upon the sleep-motion genetic data. The method also includes generating, by the processor, a user sleep duration estimate based at least in part upon the corrected wakeful period identification. Such embodiments can provide accurate and reliable measurements of sleep duration and avoid erroneous readings due to variable limb movements during sleep.

Embodiments of the invention are directed to a system for optimizing sleep patterns. A non-limiting example of the system includes a plurality of IoT sensors. The system can also include a genetic information database. The system can also include a sleep analytics engine in communication with the plurality of IoT sensors and the genetic information database. The system can also include an output interface. Such embodiments can provide convenient sleep optimization without need for clinical settings or cumbersome equipment.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The subject matter of the present invention is particularly pointed out and distinctly claimed in the claims at the conclusion of the specification. The foregoing and other features and advantages of the one or more embodiments described herein are apparent from the following detailed description taken in conjunction with the accompanying drawings in which:

Figure 1:
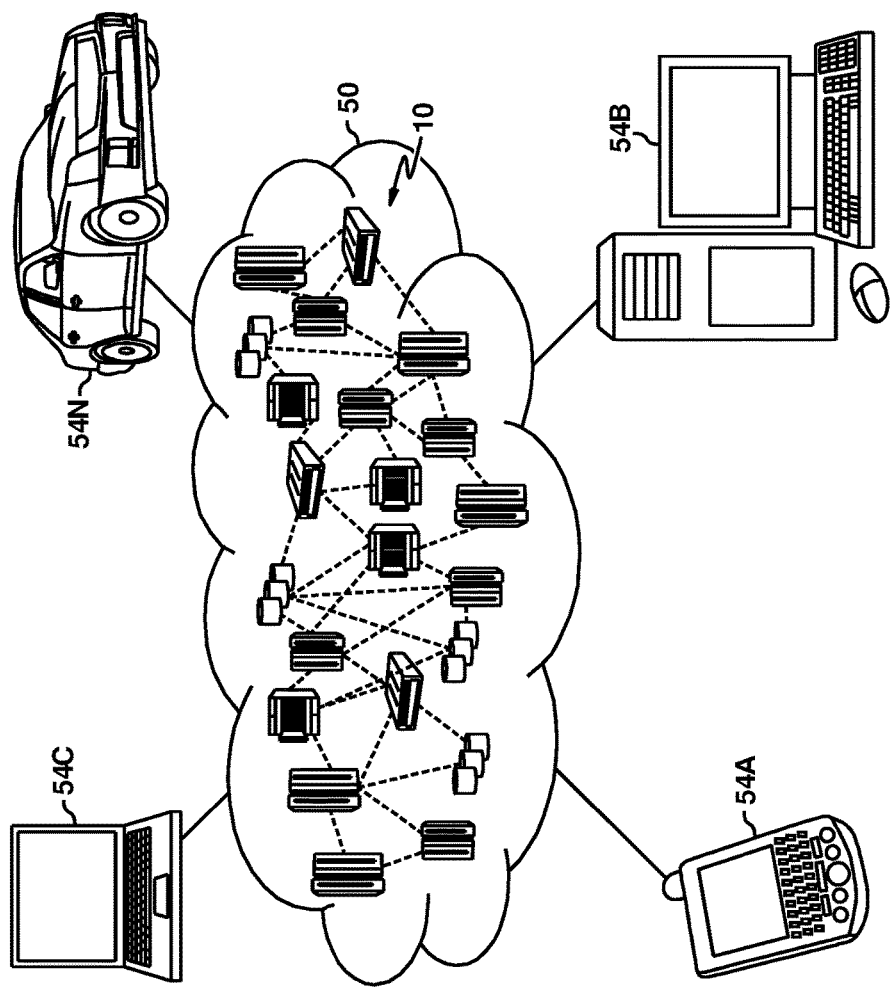
FIG. 1 depicts a cloud computing environment according to an embodiment of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can include any integer number greater than or equal to one, i.e. one, two, three, four, etc. The terms "a plurality" can include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Referring now to FIG. 1, illustrative cloud computing environment 50 according to one or more embodiments of the present invention is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
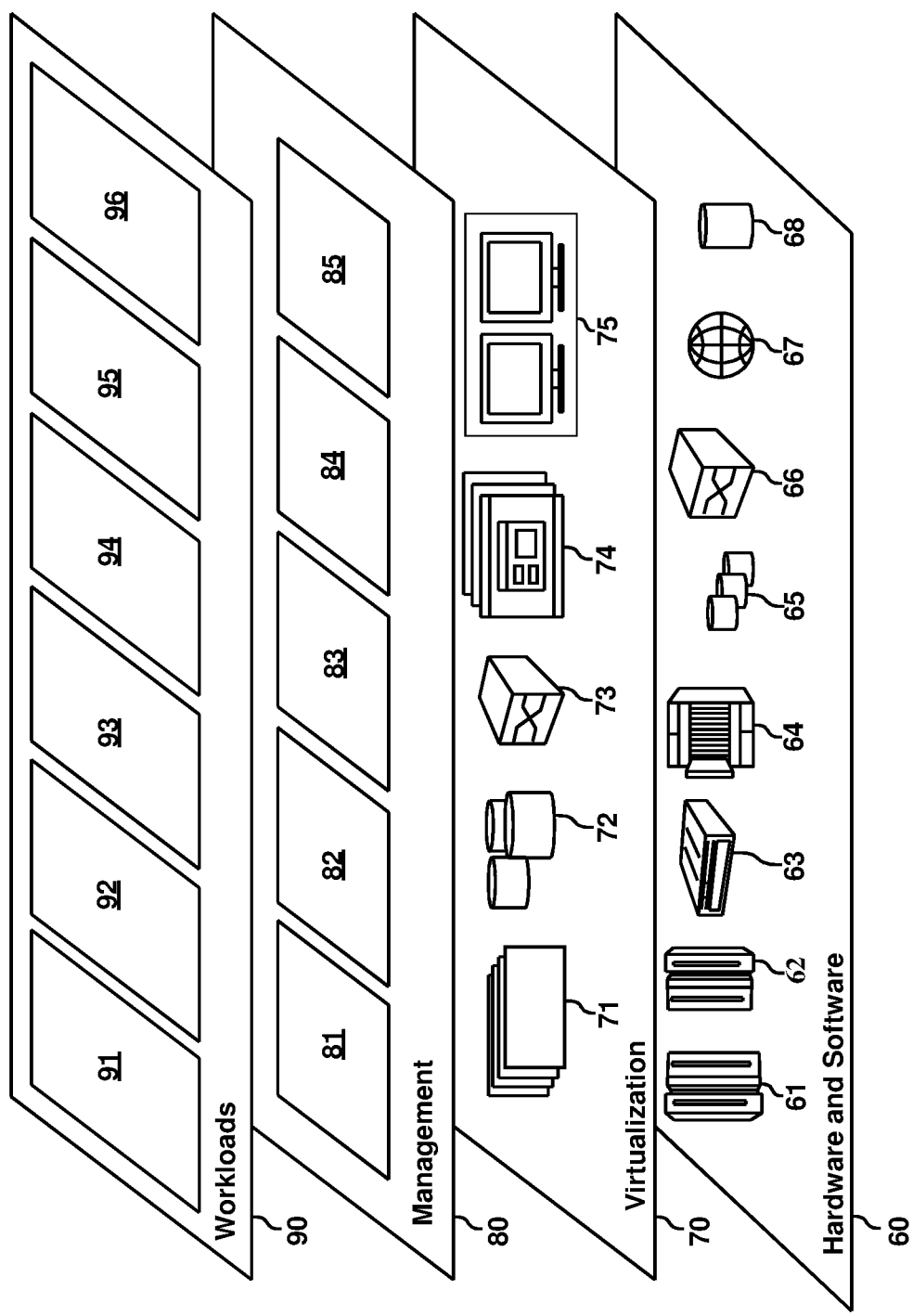
FIG. 2 depicts abstraction model layers according to an embodiment of the present invention.

Referring now to FIG. 2, a set of functional abstraction layers provided by cloud computing environment 50 (FIG. 1) according to one or more embodiments of the present invention is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments of the invention, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and optimizing individual sleep patterns 96.

Figure 3:
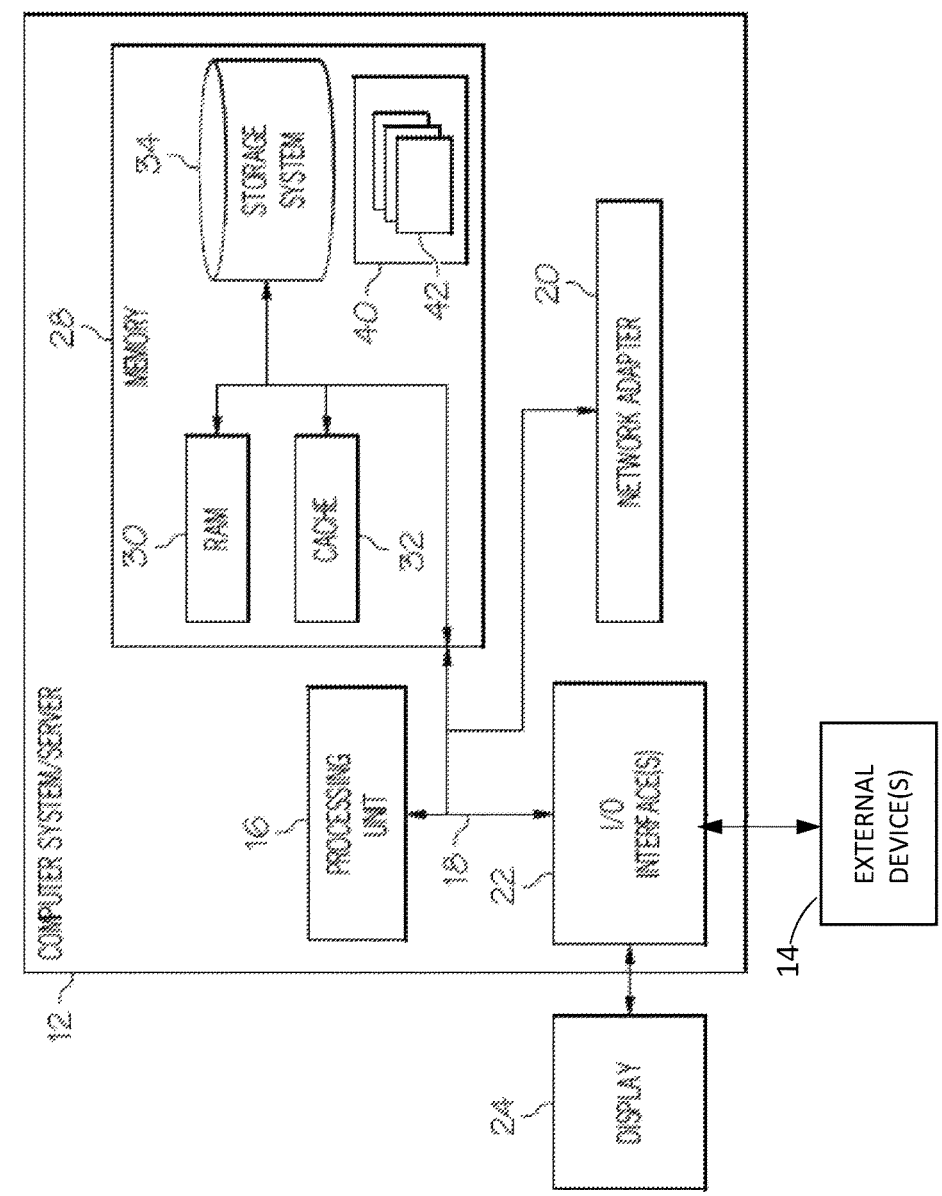
FIG. 3 depicts a computer system according to one or more embodiments of the present invention.

Referring now to FIG. 3, a schematic of a cloud computing node 100 included in a distributed cloud environment or cloud service network is shown according to one or more embodiments of the present invention. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out one or more functions and/or methodologies in accordance with some embodiments of the present invention.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of technologies that are more specifically relevant to aspects of the invention, the quality and duration of sleep on a daily basis and over time can be a critical influence on the health, productivity, and safety of individuals. Lack of sleep, for example, is frequently associated with poor performance at work or school. Moreover, persistent patterns of poor or insufficient sleep can adversely impact health and well-being.

Accurate and reliable sleep measurement and optimization has potential to benefit the health and well-being of a large population of individuals. A sufficient amount of sleep, for example, is required for optimal brain function, attention, and memory, and can also contribute to proper immune function, weight management and mood. Tracking and optimizing sleep patterns is not only of interest to individuals, for instance who wish to ensure their own individual optimal health and brain function, but also to employers, teachers, and the population at large, where inattentiveness and cognitive impairments can detrimentally impact the workplace, classrooms, and even road safety.

The quantity of sleep required for optimal performance and functioning can vary from person to person and can be impacted by genetic and environmental factors. For instance, it is widely understood that some individuals require only 7 hours of sleep per night, while others can require 8 hours of sleep per night.

In addition, for any given individual, the duration and quality of sleep on a day to day basis can be influenced by a number of environmental factors including, for instance, light exposure, caffeine consumption, and physical exertion. For example, it is known that physical exertion during the day can increase the amount of sleep required for optimal functioning. Increased physical exertion can also be associated with a better quality of sleep. Moreover, exposure to light, including light of certain characteristics such as frequency or intensity, both during sleep and before sleep can detrimentally impact the quality and quantity, or duration, of sleep for an individual. For example, exposure to high frequency and/or high intensity light two to three hours before sleep can be associated with lower melatonin levels. Lower melatonin levels can decrease the quality of sleep. In addition, periods of wakefulness and sleep can fluctuate over the course of a night for some people as well as movement during times of sleep.

A number of genetic factors can affect sleep. Individuals with a variant in the limb-movement associated genes, such as BTB Domain Containing 9 (BTBD9) gene for example, tend to move their limbs more during sleep in relation to individuals without the variant (e.g., 12 movement periods per night versus 7 movement periods). Individuals with a variant in the adenosine deaminase (ADA) gene (e.g., rs73598374 polymorphism) can have higher adenosine levels and, as a result, can experience higher quality sleep in relation to individuals without the ADA variant. In addition, individuals with a variant in the ADA gene can require relatively larger quantities of sleep in a given night than those without the variant. The cytochrome P450 1A2 (CYP1A2) gene and aryl hydrocarbon receptor gene (AHR) gene can also affect sleep through metabolism of caffeine. Specifically, individuals with a variant in one of the CYP1A2 gene or the AHR gene can metabolize caffeine at twice the rate of those with no variant in either gene. Individuals with variants in both of the CYP1A and AHR genes can metabolize caffeine at four times the rate of those with no variant in either gene.

Genetic factors can play a role in both individualized sleep requirements and also in obtaining accurate measurements. For example, caffeine consumption is widely known to impact sleep, but recent studies have shown that some individuals can be genetically predisposed to metabolize caffeine more quickly than others. In addition, studies have associated variants in an ADA gene with more intense deep sleep and, at the same time, less movement during periods of sleep.

An accurate measurement of the duration of sleep can contribute to a reliable sleep optimization system. For instance, the duration and/or quantity of sleep of an individual on an ongoing basis can aid in determining not only the presence or absence of a sleep deficit, but can provide an assessment of the amount of sleep needed for an individual.

Although accurate measurements of the quantity and/or duration of sleep can be important, such measurements can be difficult to obtain outside of a clinical or controlled setting. Internet of Things (IoT) devices can include a variety of information gathering or sensing components, such as motion sensors, accelerometers, heart rate monitors, and light sensors, that can aid in the measurement of factors pertaining to sleep. The IoT is an object-interconnecting network that can include various sensing devices. Wearable or nearby motion sensing devices, for example, can identify and associate periods of inactivity with periods of sleep. However, erroneous readings can result, for instance, where individuals experience movement during sleep if the motion sensing device associates such sleep-movements with periods of wakefulness.

In addition, because of the individualized nature of various aspects pertaining to sleep quality and quantity, providing reliable recommendations to optimize sleep patterns remains challenging.

Turning now to an overview of the aspects of the invention, one or more embodiments of the invention address the above-described shortcomings of the prior art by providing sleep monitoring that tracks motion over a period of time and corrects observed motion for genetic factors pertaining to sleep movement, such as the BTBD9 gene. Embodiments of the invention can provide an assessment of sleep quality that considers genetic factors, such as the presence or absence of a variant in the ADA gene. Embodiments of the invention can optimize sleep patterns by providing individualized sleep recommendations based upon individualized genetic information, environmental information, and/or daily activity information.

The above-described aspects of the invention address the shortcomings of the prior art by providing more accurate or reliable individualized measurements of sleep quantity and/or quality. Embodiments of the invention can optimize individual sleep patterns by generating personalized recommendations that include recommended sleep quantity, caffeine consumption guidelines, physical exertion and/or light exposure guidelines. Embodiments of the invention can provide a reliable identification of a sleep deficit.

Figure 4:
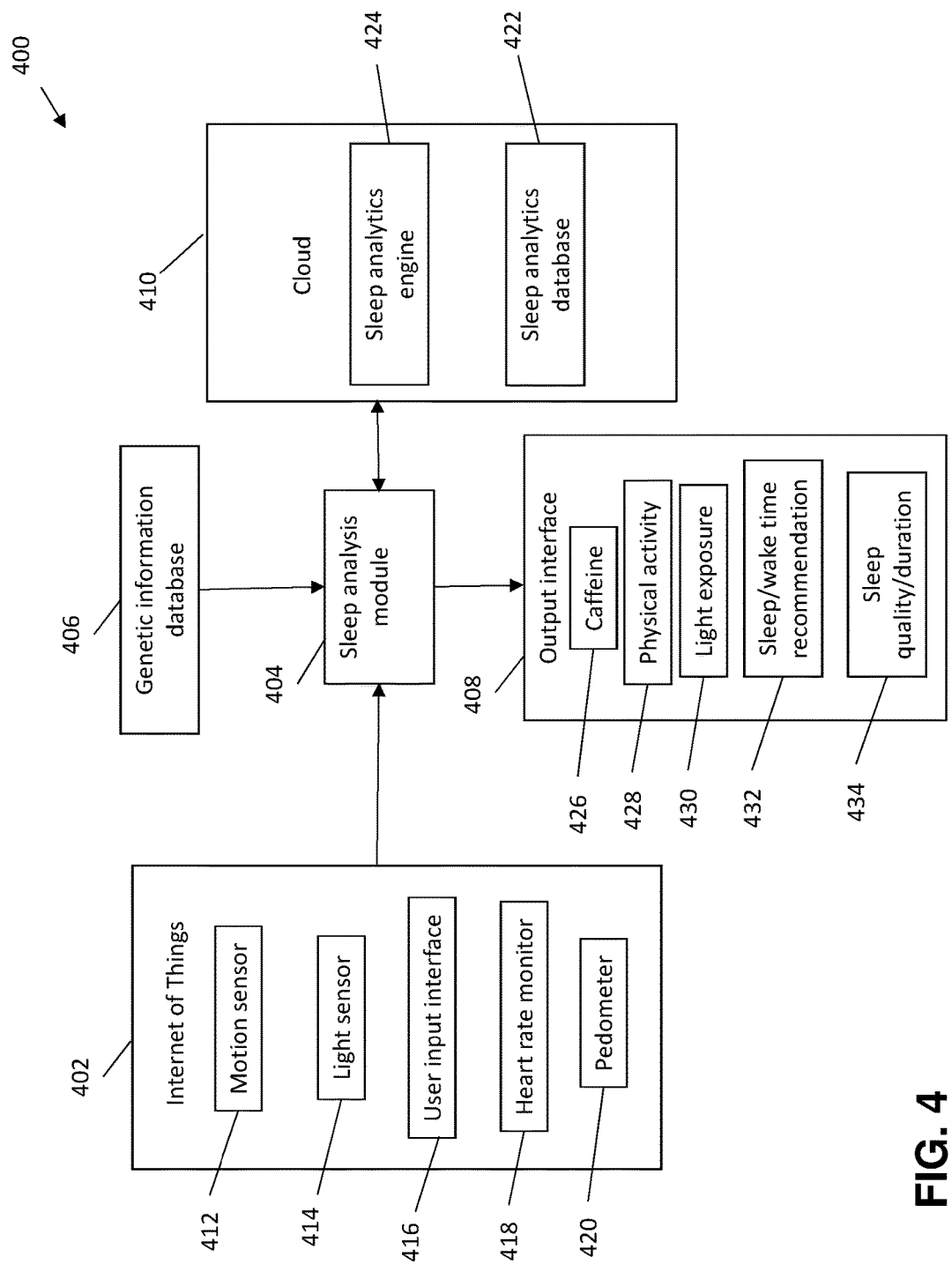
FIG. 4 depicts a diagram illustrating an exemplary system for optimizing sleep patterns according to one or more embodiments of the present invention.

Referring now to FIG. 4, a diagram illustrating an exemplary system 400 for optimizing sleep patterns according to one or more embodiments of the present invention is shown. The system 400 can include an internet of things (IoT) 402. The internet of things 402 can include an inter-connected network of devices including a plurality of sensors. The IoT 402 can include, for example, one or more of a motion sensor 412, light sensor 414, user input interface 416, heart rate monitor 418, or pedometer 420. The system 400 can include a sleep analysis module 404 in communication with the IoT 402. The sleep analysis module 404 is optionally in communication with a genetic information database 406. The sleep analysis module 404 can communicate with or can be included in whole or part in the cloud 410. The sleep analysis module 404 interacts with a sleep analytics engine 424. The sleep analytics engine 424 can communicate with a sleep analytics database 422, which can store data pertaining to sleep analysis, including analysis data, sleep measurements, and sleep recommendations for the user and optionally for other users, such as users with similar demographic or genetic profiles. In some embodiments of the invention, the sleep analytics engine 424 and sleep analytics database 422 are in the cloud 410.

The motion sensor 412 can include any sensor capable of detecting user body movement, such as an accelerometer, gyroscope, compass, pressure sensor, light-based sensors, or combinations thereof. The motion sensor 412 can be included in one or more devices in the IoT 402, such as smart phones, wearable devices such as smart watches or wearable wrist bands, or stand-alone devices. The IoT can include wired or wireless communication between a plurality of devices, including, for instance, Bluetooth, near-field communication (NFC), Wi-Fi, radio-frequency (RF), Ethernet, and the like.

The light sensor 414 can include sensors that detect light frequency and/or light intensity. In embodiments of the invention, the IoT 402 can include one or more other sensors, including any other sensors that can be useful in assessing sleep movement, physical exertion, and/or external or environmental conditions, such as thermometers, hygrometers, barometers, or microphones.

The user input interface 416 can include a keyboard, touch sensitive display, microphone, or other means for providing input to the system 400. The user input interface 416, in some embodiments of the invention, can receive caffeine intake data for a user, for example by manual input from a user when caffeine is consumed.

In embodiments of the invention, the genetic information database 406 includes genetic information for the user. The genetic information in the genetic information database 406 can be in the form of gene sequences or in the form of identification of a presence or absence of specific gene variants. The genetic information can include, for example, information identifying variants in the BTBD9 gene, the ADA gene, the CYP1A2 gene, and/or the AHR gene for a user. In some embodiments of the invention, access to the genetic information database 406 can be controlled, restricted, or secured to protect user privacy.

The sleep analytics engine 424 can perform analytics and/or machine learning techniques. The sleep analytics engine 424 can correlate descriptors from sensor and genetic information using known methods, such as multiple linear regression, partial least squares fit, Support Vector Machines, and random forest. The sleep analytics engine 424 can generate sleep measurements and/or sleep recommendations.

Figure 5:
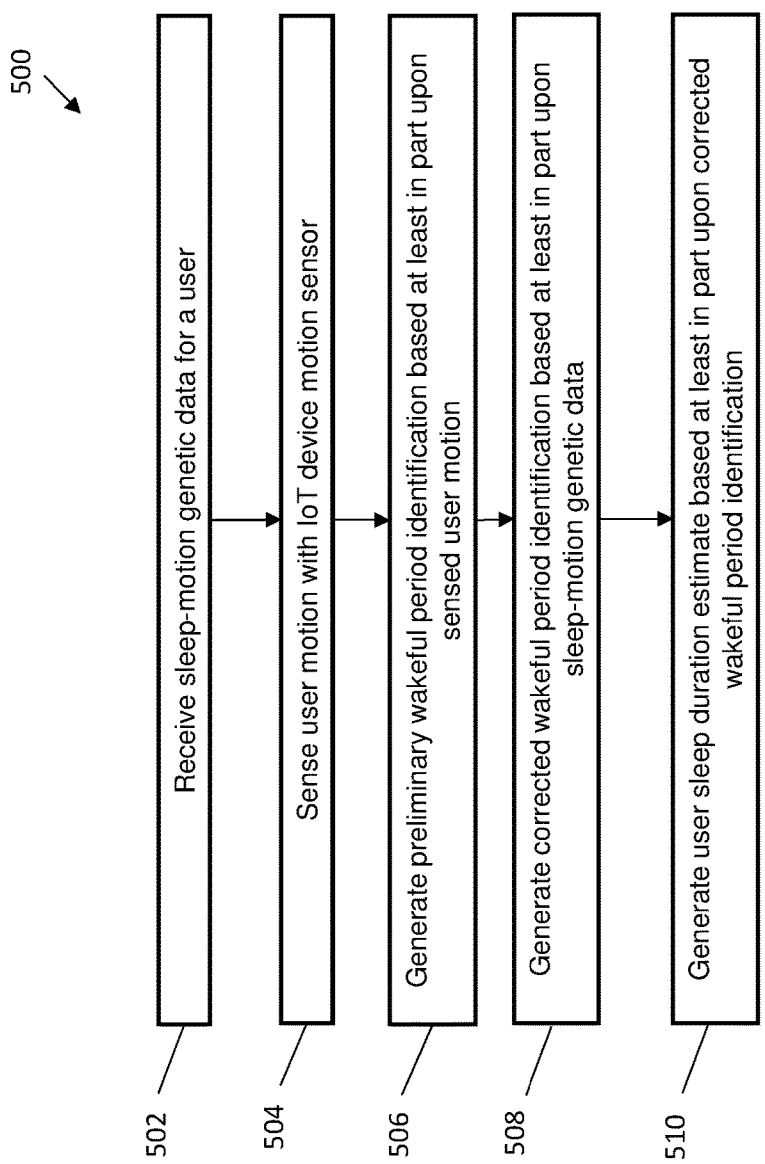
FIG. 5 is a flow diagram illustrating a method for generating a sleep duration estimate according to one or more embodiments of the present invention.

FIG. 5 depicts a flow chart of an exemplary method 500 for generating a user sleep duration estimate according to one or more embodiments of the present invention. The method 500 includes, as shown at block 502, receiving sleep-motion genetic data for a user. Sleep-motion genetic data can include, for example, an identification of the presence or absence of a gene polymorphism that is associated with limb movement during sleep, such as a polymorphism in BTBD9, TOX3, BC034767, MEIS1, MAP2K/SKOR1, or PTPRD. The method 500 also includes, as shown at block 504, sensing user motion with an IoT motion sensor. The method 500 also includes, as shown at block 506, generating a preliminary wakeful period identification based at least in part upon the sensed user motion. The method 500 also includes, as shown at block 508 generating a corrected wakeful period identification based at least in part upon sleep-motion genetic data. The method 500 also includes, as shown at block 510, generating a user sleep duration estimate based at least in part upon the corrected wakeful period identification.

Figure 6:
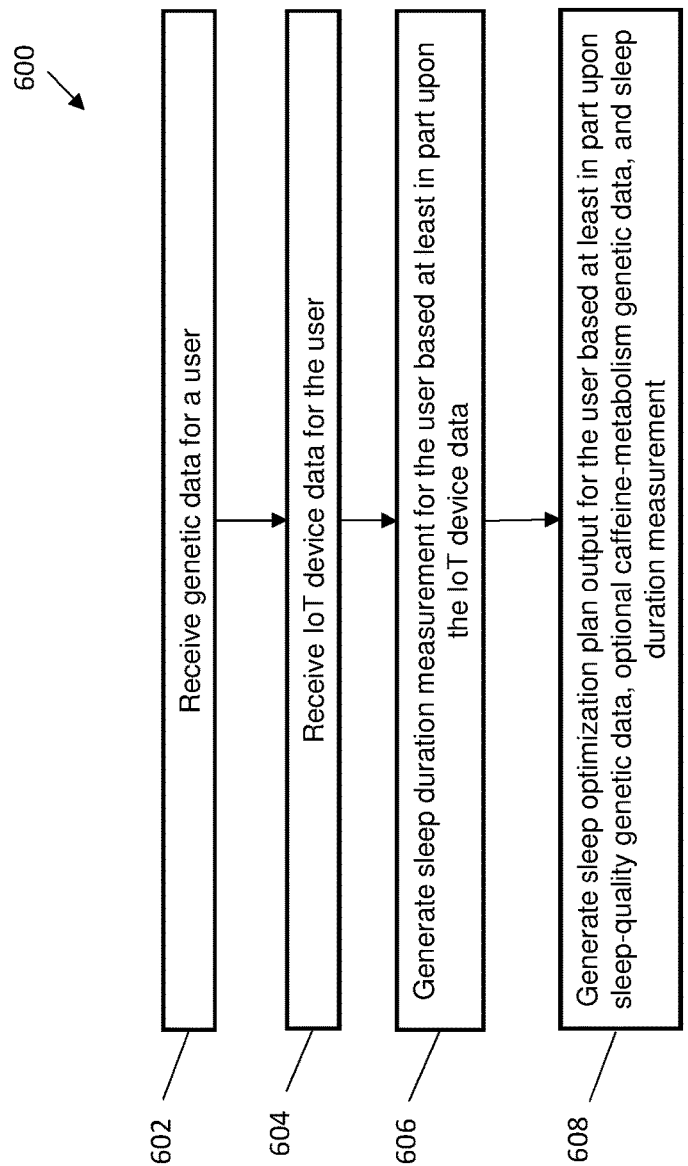
FIG. 6 is a flow diagram illustrating a method for generating a sleep optimization plan according to one or more embodiments of the present invention.

FIG. 6 depicts a flow chart of an exemplary method 600 for optimizing sleep patterns according to one or more embodiments of the present invention. The method 600 includes, as shown at block 602, receiving sleep-quality genetic data for a user. Sleep-quality genetic data can include, for example, an identification of the presence or absence of a gene polymorphism that is associated with sleep quality for a user, such as a polymorphism (rs73598374) in adenosine deaminase (ADA). The method 600 also includes, as shown at block 604, receiving caffeine-metabolism genetic data for the user. Caffeine-metabolism genetic data can include, for example, an identification of the presence or absence of a gene polymorphism that is associated with caffeine metabolism for a user, such as a polymorphism in CYP1A2 and/or AHR genes. The method 600 also includes, as shown at block 606 receiving a sleep duration measurement for the user. In some embodiments of the invention, the method includes receiving a plurality of sleep duration measurements or a pattern of sleep duration for the user. The method 600 also includes, as shown at block 608 generating a sleep optimization plan output for the user based at least in part upon the sleep-quality genetic data, the caffeine metabolism genetic data, and/or the sleep duration measurement.

Figure 7:
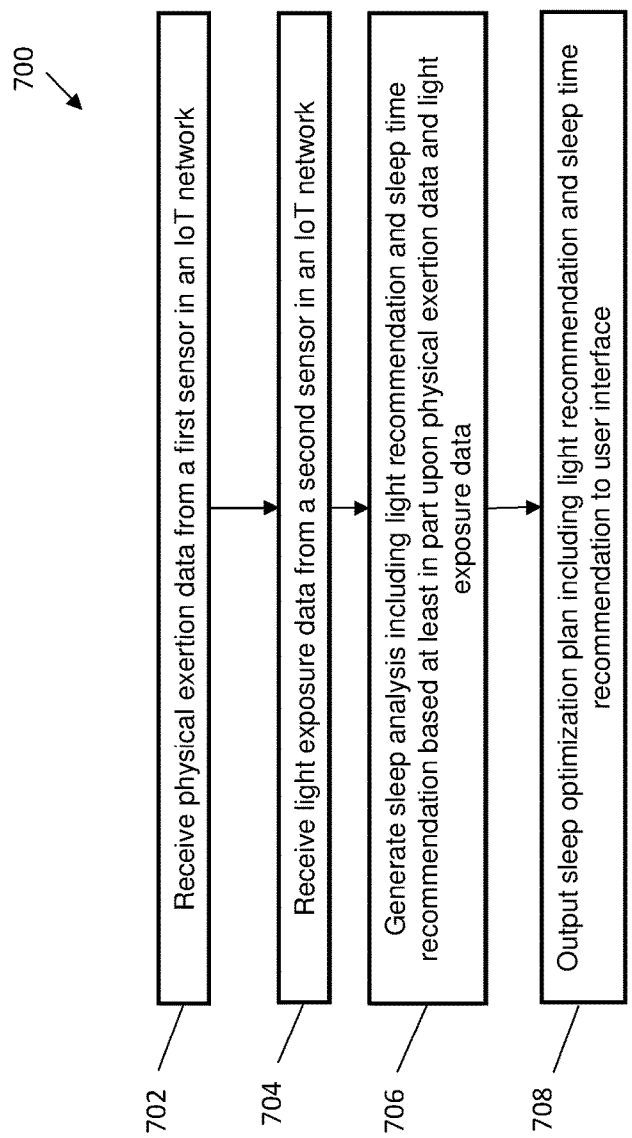
FIG. 7 is a flow diagram illustrating another method for generating a sleep optimization plan according to one or more embodiments of the present invention.

FIG. 7 depicts a flow chart of another exemplary method 700 for optimizing sleep patterns according to one or more embodiments of the present invention. The method 700 includes, as shown at block 702, receiving physical exertion data from a first sensor in an IoT network. The physical exertion data can include, for example, heart rate data, accelerometer data, gyroscope data, altimeter data, temperature sensor data, bioimpedance data, and combinations thereof. The method 700 also includes, as shown at block 704, receiving light exposure data from a second sensor in an IoT network. The light exposure data can include, for example, light frequency and/or light intensity measurements. The light exposure data can be limited to a specific time range, for example to a time range associated with sleep of the user or with an average user, such as in the evening or at night or within 2 or 3 hours of bedtime for the user or for an average user. The method 700 also includes, as shown at block 706, generating a sleep analysis including a light recommendation and a sleep time recommendation based at least in part upon the physical exertion data and the light exposure data. The sleep analysis can include a determination of whether sleep patterns are likely to be impacted by light exposure, physical exertion, or other factors. The method 700 also includes, as shown at block 708 outputting the sleep optimization plan including a light recommendation and a sleep time recommendation to a user interface. A light recommendation can include, for example, a recommendation to avoid lighting of a given frequency or intensity within a specified time window. A sleep time recommendation can include, for example, a suggested bed time, wake time, number of hours of sleep, or both.

In an exemplary scenario, a method can include receiving physical exertion data during the day and classifying the physical exertion data, for instance using sleep analytics engine, as low, medium, or high). The exemplary method can include receiving light exposure data within three hours before sleep onset and classifying the light exposure data as low, medium, or high. The exemplary method can include receiving daily caffeine intake data and classifying the daily caffeine intake data as low, medium, or high, for instance, relative to the user's historical caffeine consumption, relative to a threshold caffeine value, or relative to a level derived from a plurality of individuals, such as an average user or an average user with a similar demographic or genetic profile. Optionally, the method can include receiving, with user consent, genetic information identifying variants in BTBD9, ADA, CYP1A2, and AHR. Exemplary data and exemplary sleep optimization plans for the exemplary data are summarized in the following table.

| Physical exertion | Light exposure | Caffeine intake | BTBD9 variant | ADA variant | CYP1A2 variant | AHR variant | Output measurement and plan |
|---|---|---|---|---|---|---|---|
| High | High | High | Yes | No | Yes | Yes | Adjust sleep duration upward due to BTBD9 No caffeine recommendation based on genetic data Recommend reducing light exposure before sleep |

-continued

| Physical exertion | Light exposure | Caffeine intake | BTBD9 variant | ADA variant | CYP1A2 variant | AHR variant | Output measurement and plan |
|---|---|---|---|---|---|---|---|
| Low | Medium | Medium | No | Yes | No | No | Adjust sleep duration downward due to BTBD9 Increase total sleep duration requirement due to ADA Recommend increased physical activity and lower caffeine |
| Medium | High | Medium | Yes | Yes | Yes | Yes | Adjust sleep duration upward due to BTBD9 No caffeine recommendation based on genetic data Recommend reducing light exposure before sleep |
| Low | Low | High | N/A | N/A | N/A | N/A | Recommend increased physical activity and lower caffeine |
| High | High | Medium | N/A | N/A | N/A | N/A | Recommend decreased light exposure and lower caffeine |
| Low | High | Low | N/A | N/A | N/A | N/A | Recommend increased physical activity and decreased light exposure |

Embodiments of the present invention can provide accurate sleep duration estimates by incorporating genetic data in a motion-based analysis. Embodiments of the invention can also provide individualized sleep optimization plans that consider daily environmental factors, such as light exposure, genetic information, such as caffeine metabolism information, and/or personalized activity information, such as daily physical exertion data. Embodiments of the invention can provide individualized and reliable plans for optimizing the duration and quality of sleep for a user without clinical intervention or cumbersome equipment.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments of the invention, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There can be many variations to this diagram or the steps (or operations) described therein without departing from the spirit of embodiments of the invention. For instance, the steps can be performed in a differing order or steps can be added, deleted or modified. All of these variations are considered a part of the claimed invention.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for generating a sleep optimization plan, the method comprising:
   receiving, by a processor, genetic data for a user, the genetic data comprising a presence of a gene polymorphism in BTBD9, TOX3, BC034767, MEIS1, MAP2K/SKOR1, or PTPRD;
   receiving, by the processor, Internet of Things (IoT) device data for the user;
   generating, by the processor, a sleep duration measurement for the user based at last in part upon the IoT device data;
   correcting the sleep duration measurement based on the presence of the gene polymorphism; and
   generating, by the processor, a sleep optimization plan for the user based at least in part upon the genetic data and the corrected sleep duration measurement.

2. The computer-implemented method of claim 1, wherein the genetic data is sleep-quality genetic data.

3. The computer-implemented method of claim 1, wherein the sleep-quality genetic data comprises a determination of a presence or an absence of a polymorphism in adenosine deaminase.

4. The computer-implemented method of claim 1, wherein the IoT device data comprises physical exertion data for the user.

5. The computer-implemented method of claim 1, wherein the physical exertion data comprises data from the group consisting of heart rate data, accelerometer data, gyroscope data, altimeter data, temperature sensor data, bioimpedance data, and combinations thereof.

6. The computer-implemented method of claim 1, wherein the IoT device data comprises light exposure data.

7. The computer-implemented method of claim 1 further comprising receiving, by the processor, caffeine intake data for the user.

8. The computer-implemented method of claim 1 further comprising receiving, by the processor, caffeine-metabolism genetic data for the user.

9. The computer-implemented method of claim 1, wherein the caffeine-metabolism genetic data comprises a determination of a presence or an absence in a polymorphism in a cytochrome P450 1A2 gene, an aryl hydrocarbon receptor gene, or both.

10. The computer-implemented method of claim 1 further comprising generating the sleep optimization plan in a cloud environment.

11. A computer-implemented method for generating a sleep duration estimate, the method comprising:
    receiving, by a processor, sleep-motion genetic data for a user, the sleep-motion genetic data comprising a presence of a gene polymorphism in BTBD9, TOX3, BC034767, MEIS1, MAP2K/SKOR1, or PTPRD;
    sensing, by a motion sensor in an IoT network, user motion;
    generating, by the processor, a preliminary wakeful period identification based at least in part upon the sensed user motion;
    generating, by the processor, a corrected wakeful period identification based at least in part upon the presence of the gene polymorphism in the sleep-motion genetic data; and
    generating, by the processor, a user sleep duration estimate based at least in part upon the corrected wakeful period identification.

12. The computer-implemented method of claim 11, wherein the sleep-motion genetic data comprises a determination of a presence or absence of a polymorphism in a BTB Domain Containing 9 (BTBD9) gene.

* * * * *